(12) United States Patent
Predieri

(10) Patent No.: US 11,013,813 B2
(45) Date of Patent: May 25, 2021

(54) CONJUGATES OF STANOZOLOL AND HYALURONIC ACID

(71) Applicant: ACME DRUGS S.R.L., Cavriago (IT)

(72) Inventor: Paolo Giulio Predieri, Cavriago (IT)

(73) Assignee: ACME DRUGS S.R.L., Cavriago (IT)

( * ) Notice: Subject to any disclaimer, the term of this patent is extended or adjusted under 35 U.S.C. 154(b) by 0 days.

(21) Appl. No.: 16/981,810

(22) PCT Filed: Mar. 13, 2019

(86) PCT No.: PCT/IB2019/052034
§ 371 (c)(1),
(2) Date: Sep. 17, 2020

(87) PCT Pub. No.: WO2019/180548
PCT Pub. Date: Sep. 26, 2019

(65) Prior Publication Data
US 2021/0038735 A1    Feb. 11, 2021

(30) Foreign Application Priority Data
Mar. 21, 2018  (IT) .......................... 102018000003841

(51) Int. Cl.
*A61K 47/61* (2017.01)
*A61K 9/00* (2006.01)
*A61K 31/58* (2006.01)
*A61K 47/69* (2017.01)

(52) U.S. Cl.
CPC ............ *A61K 47/61* (2017.08); *A61K 9/0048* (2013.01); *A61K 31/58* (2013.01); *A61K 47/6903* (2017.08)

(58) Field of Classification Search
CPC .... A61K 47/61; A61K 47/6903; A61K 31/58; A61K 9/0048
See application file for complete search history.

(56) References Cited

FOREIGN PATENT DOCUMENTS

| EP | 1891940 A1 * | 2/2008 |
| EP | 2894173 A1 | 7/2015 |

OTHER PUBLICATIONS

Tamura et al, Novel hyaluronic acid-methotrexate conjugate suppresses joint inflammation in the rat knee: efficacy and safety evaluation in two rat arthritis models ,Arthritis Res Ther; 18: 79. (Year: 2016).*
Search Report and Written Opinion of PCT/IB2019/052034 dated Jul. 5, 2019.

* cited by examiner

*Primary Examiner* — Carlos A Azpuru
(74) *Attorney, Agent, or Firm* — Silvia Salvadori, P.C.; Silvia Salvadori

(57) ABSTRACT

Disclosed are conjugates between stanozolol and hyaluronic acid or a hyaluronic acid salt, characterised in that stanozolol is conjugated with the carboxyl group of hyaluronic acid or the hyaluronic acid salt via a spacer that forms an ester bond with the hydroxyl group of stanozolol and an ester or amide bond with the carboxyl group of hyaluronic acid or the hyaluronic acid salt. The conjugates according to the invention are useful to prepare hydrogels, injectable hydrogels, hydrogels for external use, creams, lotions, foams, aqueous solutions for intra-articular use, emulsions for ophthalmic use, eyedrops, scaffolds, artificial tissues and culture media.

7 Claims, No Drawings

CONJUGATES OF STANOZOLOL AND HYALURONIC ACID

This application is a U.S. national stage of PCT/IB2019/052034 filed on 13 Mar. 2019, which claims priority to and the benefit of Italian Application No. 102018000003841 filed on 21 Mar. 2018, the contents of which are incorporated herein by reference in their entireties.

The invention relates to conjugates between stanozolol and hyaluronic acid or a hyaluronic acid salt, characterised in that stanozolol is conjugated with the carboxyl group of hyaluronic acid or the hyaluronic acid salt via a spacer that forms an ester bond with the hydroxyl group of stanozolol and an ester or amide bond with the carboxyl group of hyaluronic acid or the hyaluronic acid salt.

PRIOR ART

Hyaluronic acid is the main component of synovial fluid. Intra-articular administration of hyaluronic acid, known as viscosupplementation, has received widespread support for the treatment of mild and moderate osteoarthritis of the knee and other joints (Henrotin Y, et al., *Semin Arthritis Rheum.* 2015 October; 45(2):140-9. doi: 10.1016/j.semarthrit.2015.04.011) because it is safe, reduces pain, and improves joint mobility. High-molecular-weight hyaluronic acid has anti-inflammatory properties, as it induces a macrophage phenotype that stimulates tissue repair by expressing genes such as arg1, IL-10 and mrc1 (Rayahin J E, et al., *ACS Biomater Sci Eng.* 2015 Jul. 13; 1(7):481-493)), and exerts chondroprotective effects (Bauer C, et al., *J Inflamm* (Lond). 2016 Sep. 13; 13(1):31. doi: 10.1186/s12950-016-0139-y).

Hyaluronic acid is used in the production of medical devices and proprietary medicinal products for intra-articular and intravenous use, and is also used to prepare eyedrops, gels and artificial tears for ophthalmic use with the purpose of hydrating and lubricating the cornea and conjunctival mucosa.

Stanozolol is a synthetic steroid which has long been used in veterinary medicine in cachectic states of animals due to its anabolic and orexigenic effects. Unfortunately, stanozolol is substantially insoluble in water, and only slightly soluble in acetone. The fact that it is only soluble in solvents that are poorly tolerated or irritants, if not actually toxic to tissues and organisms, has limited the possibilities of therapeutic exploitation of stanozolol, with the result that they are restricted to disorders that can be treated with aqueous suspensions and tablets. Unfortunately, suspensions and tablets do not fully exploit the therapeutic potential that stanozolol could have if it were rendered water-soluble so that it could be administered or used in other pharmaceutical forms, medical devices, scaffolds and culture media.

Some important properties that clearly distinguish stanozolol from other androgenic-anabolic steroids (AAS) were recently highlighted. Unlike natural androgens and other AAS's, stanozolol interacts with glucocorticoid receptors (GRs) and the progesterone receptor via a high-affinity bond. From the clinical standpoint, the action of stanozolol can therefore be defined as not only anabolic-myotrophic, but above all anti-dystrophic. In vitro studies of fibroblast cell cultures have demonstrated that stanozolol increases collagen synthesis with dose-dependent dynamics by producing transforming growth factor B1 (TGF-beta1), thus promoting tissue growth and repair (V. Falanga, et al., *J Invest Dermatol,* 111 (1998), pp. 1193-1197). Stanozolol has already been used orally in the treatment of tracheal collapse in dogs, wherein its efficacy and safety have been demonstrated (Adamama-Moraitou, K K, et al. (2011). *International Journal of Immunopathology and Pharmacology* 24(1): 111-118). The results of an in vivo study obtained by intra-articular administration demonstrate a specific regenerative action for cartilage tissue, which promotes hyperplasia of the synoviocytes and the appearance of proliferating chondroblast groups (Spadari A, et al., *Res vet Sci* 2013;94:379-87); moreover, when given by intra-articular administration, it reduces lameness in horses with osteoarthritis (Spadari A, et al., *J Equine Vet Sci* 2015; 35:105-10). However, intra-articular injection of stanozolol in the form of suspensions (stanozolol crystals or microcrystals suspended in the carrier) involves the following drawbacks:

it exerts an undesirable abrasive effect on the soft tissues of the joint and joint cartilage;

it attracts macrophages (especially neutrophils) from the bloodstream into the joint cavity, leading to serious inflammatory reactions;

the high clearance gives rise to a rapid, massive exit of stanozolol from the joint cavity;

the sudden movement of stanozolol from the joint to the bloodstream limits its direct effects on the target joint tissues, thus weakening its joint-tissue regeneration potential;

the rapid disappearance of stanozolol from the joint cavity requires frequent injections (at least one injection a week is required to maintain adequate concentrations in the synovial fluid), involving obvious drawbacks in terms of compliance and the risk of undesirable systemic side effects (hormonal action on non-target organs).

The wound-healing and re-epithelialising properties of stanozolol cannot be fully exploited in the ophthalmic field, because instillation of its suspensions into the conjunctival sac would involve the risk of corneal and conjunctival abrasions.

There is consequently a need for a hydrophilic derivative of stanozolol that can be retained in the joint cavity, ocular cavity or scaffold matrix, and can render the steroid gradually bioavailable to the surrounding tissues such as cartilage, bone, synovial, ligament and corneal tissues, maximising its local effects.

DESCRIPTION OF THE INVENTION

It has now been found that the drawbacks discussed above can be eliminated by conjugating stanozolol with hyaluronic acid via a spacer that forms an ester bond with the hydroxyl group of stanozolol and an ester or amide bond with the carboxyl group of hyaluronic acid or the hyaluronic acid salt.

The preferred conjugates according to the invention are represented by formula (I)

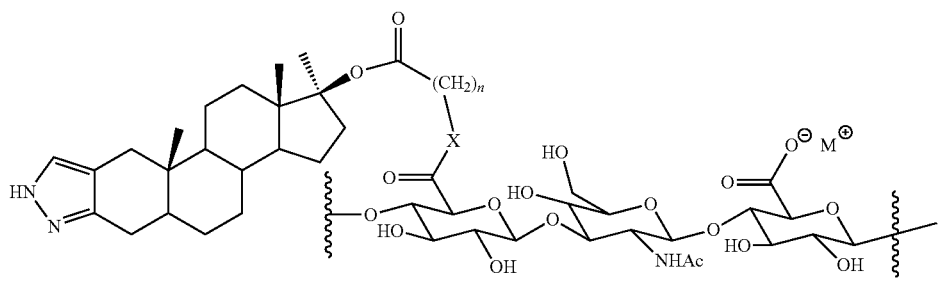

(I)

wherein:

n=1-12;

X is a bivalent group selected from —O— and —NH—;

$M^+$ represents a proton or cation of an alkali metal;

the group

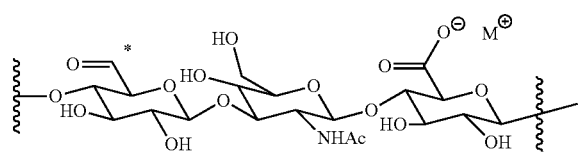

represents the repeating unit of hyaluronic acid or a salt thereof with an alkali metal, wherein the symbol * indicates the carbon atom of said repeating unit bonded to the X group.

X is preferably —O— and n is preferably 2, 3, 4 or 5.

The hyaluronic acid used in the present invention has a molecular weight ranging from 1,000 to 10,000,000 Da, preferably 5,000 to 8,000,000 Da, most preferably 30,000 to 1,000,000 Da.

Hyaluronic acid can be obtained by processes of extraction, fermentation or biosynthesis.

In the conjugates according to the invention, stanozolol and hyaluronic acid are not bonded to one another directly, but via a spacer that forms a covalent ester bond with the hydroxyl group of stanozolol, and an ester or amide bond with the carboxyl group of the D-glucuronic acid of the repeating unit of hyaluronic acid.

The covalent bond between the spacer and the carboxyl group of the D-glucuronic acid of the repeating unit of hyaluronic acid involves a percentage of 1% to 90% (degree of substitution) of the carboxyl groups present. The degree of substitution is preferably between 1-50% on a molar basis, most preferably between 5 and 30%, again on a molar basis.

The conjugate between stanozolol and hyaluronic acid or a hyaluronic acid salt according to the invention is obtained by a process involving the following steps:

a) converting hyaluronic acid or an alkaline salt thereof to the corresponding tetraalkylammonium salt; hyaluronic acid sodium salt is preferably used as starting product, and is converted to the tetraalkylammonium salt, preferably the tetrabutylammonium salt, to increase its solubility in organic solvents; said conversion can be conveniently conducted with an ion-exchange resin in acid form, such as amberlite, previously converted to its tetrabutylammonium form by treatment with tetrabutylammonium hydroxide;

b) protecting the NH group of the pyrazole ring of stanozolol with an amino-protecting group, to give a compound of formula (II)

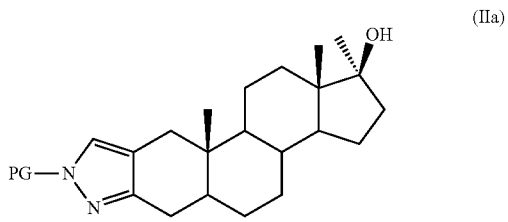

(II)

wherein PG represents an amino-protecting group such as the fluorenylmethoxycarbonyl group, which can be indiscriminately positioned on the nitrogen atom in the 1 position or the 2 position of the pyrazole ring, as represented by formulas (IIa) and (IIb) below;

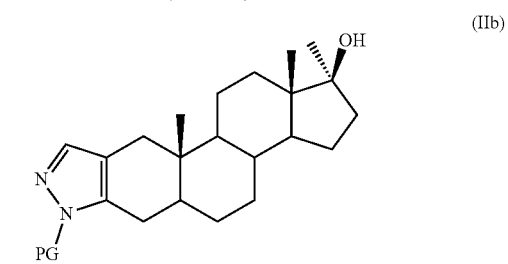

c) reacting the compound of formula (II) with a compound of formula (III)

$$A\text{-CO}-(CH_2)_n-Y \qquad (III)$$

wherein A is a halogen, n is as defined in the compounds of formula (I), and Y is a halogen, preferably bromine, or an NH-PG' group, wherein PG' is a primary amino-protecting group which can be the same as or different from PG, to give a compound of formula (IV)

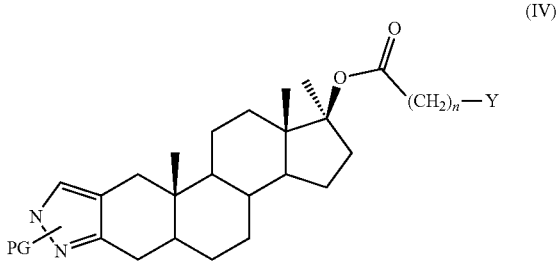

(IV)

wherein PG, n and Y are as defined above. The reaction is generally conducted at room temperature by reacting the mixture of regioisomers (IIa) and (IIb) with the acyl halide of an ω-halogen-carboxylic acid, in a solvent such as chloroform or methylene chloride, in the presence of organic bases such as pyridine and 4-dimethylaminopyridine;

d) reacting the compound of formula (IV), wherein Y is a halogen, with the hyaluronic acid tetraalkylammonium salt obtained in step a), wherein the stoichiometric ratio between the compound of formula (IV) and said tetraalkylammonium salt is such as to obtain the desired degree of substitution for the stanozolol-hyaluronic acid conjugate of formula (I), with simultaneous removal of the PG group, to give a compound of formula (I), wherein X is —O— as tetraalkylammonium salt, having the desired degree of substitution; the conjugation and removal of the protecting group are conducted in a single step, operating at room temperature in a solvent selected from dimethylsulphoxide, dimethylformamide and N-methylpyrrolidinone; or d') removing the PG' group from the compound of formula (IV), wherein Y is an NH-PG' group obtained in step c), to give the corresponding product with the deprotected primary amino group of formula (IVa)

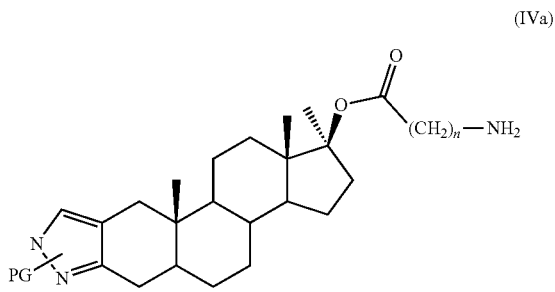

(IVa)

which can be optionally isolated, followed by reacting the compound of formula (IVa) with the carboxyl group of hyaluronic acid and a condensing agent, using a stoichiometric ratio between the compound of formula (IVa) (or the compound of formula IV wherein Y is NH-PG' if compound (IVa) is not isolated) and hyaluronic acid, so as to obtain the desired degree of substitution for the stanozolol-hyaluronic acid conjugate; under the reaction conditions, the PG group is removed in situ to give a compound of formula (I), wherein X is —NH— as acid, having the desired degree of substitution;

e) converting the product obtained in step d) or step d') to the corresponding compound of formula (I) in the form of acid or salt having the desired degree of substitution.

The use of a bifunctional spacer for the conjugation of stanozolol by acylation of its hydroxyl group solves the problem of the low reactivity of the OH group in the 17 β position of stanozolol, a tertiary group which is particularly sterically hindered and unstable in an acid medium, with consequent possible transposition reactions leading to structural variations on the C and D rings of the steroid. Stanozolol also possesses a pyrazole nitrogen that is more nucleophilic than the hydroxyl, which must be suitably protected before the subsequent O-acylation stage. The selection of the protecting group is therefore an important factor for the subsequent conjugation with hyaluronic acid and for obtaining the end product.

The conjugates according to the invention possess modulatable water solubility suitable for the production of medicaments, medical devices and scaffolds. By saturating only part of the sites where hyaluronic acid is conjugated with stanozolol, highly water-soluble hydrogels characterised by various degrees of viscoelasticity are obtained, which in turn can be used to prepare culture media, medical devices and bioavailable pharmaceutical preparations, persistent at the site of administration or use, and characterised by slow, constant release of small doses of water-soluble stanozolol in the non-crystalline molecular state.

Another object of the invention is compositions containing said conjugates as active ingredients.

The compositions according to the invention are devoid of abrasive properties, well tolerated at local and systemic levels, and guarantee a long-lasting action and a high level of clinical efficacy.

It has also been found that due to the conjugation, the doses of stanozolol can be reduced as a result of synergic effects between the ingredients of the conjugates according to the invention. Said synergic effect is greater than that observed when a mixture of stanozolol and hyaluronic acid is administered.

Moreover, the simple physical mixture of stanozolol and sodium hyaluronate in aqueous solution (suspension) is not stable, because the ingredients separate rapidly, giving rise to the formation of stanozolol deposits which are difficult to resuspend, measure and administer.

The conjugates according to the invention can be advantageously used to prepare:

scaffolds and artificial tissues consisting of organic or inorganic, porous or non-porous matrices, which are impregnated, coated or mixed with the conjugates according to the invention at different degrees of viscoelasticity, tenacity and persistence, for dental, orthopaedic, ophthalmic or neurological use or for tissue reconstruction in plastic surgery;

long-acting medicaments in aqueous solution for intra-articular slow-release of stanozolol, characterised by low joint clearance, a long-lasting local effect, high tolerability and the absence of abrasive actions;

medicaments in aqueous solution or in the form of emulsions for ophthalmic use that release stanozolol slowly in non-crystalline form, with a long-lasting effect, and no abrasive or irritant action on the tissues;

culture media suitable for regular, lengthy hormonal stimulation of the somatic cells or stem cells in the field of artificial production of cells, tissues and organs;

culture media able to guide and determine, by means of slow, regular, constant hormonal stimulation, the differentiation of stem cells towards the desired cell lines, intensifying their proliferation (e.g. production of cartilage tissue from stem cells).

The conjugates according to the invention, suitably formulated, are advantageously used for the local treatment of osteochondral defects and lesions, local treatment of tendon and ligament lesions, local (intra-articular) treatment of degenerative processes of the joint tissues (regenerative viscosupplementation), local treatment of wounds and sores, and local treatment of eye lesions (e.g. treatment of corneal lesions and post-operative management of corneal transplants). Other fields of use of the conjugates according to the invention include dentistry, surgical orthopaedics, dermatology and plastic surgery for the correction of soft tissue defects (physical and chemical burns, traumatic lesions, angioedema or Quincke's oedema, cutaneous vasculitis and thrombophlebitis).

For said applications, the conjugates will be formulated in the form of scaffolds permeated with high-viscosity hydrogels, injectable hydrogels, hydrogels for external use, creams, lotions and foams based on hydrogels, and culture media for the cultivation of artificial tissues.

In the treatment of joint lesions, the conjugates according to the invention, in hydrogel form, exert a lubricating activity on the joint tissues, a protective effect against mechanical damage caused by physical exercise on the bone heads, and a gradual, constant, controlled local release of soluble, bioavailable stanozolol, with consequent anabolic stimulation of the tissues, slowing and reduction of synovial clearance of stanozolol, and elimination or marked reduction of the undesirable systemic effects of stanozolol.

Said elimination/reduction can also take place in the event of joint clearance variations secondary to an inflammatory state of the synovial capsule.

Slow release of stanozolol from the hydrogel, and its prevalent metabolisation in the joint tissues (synovial capsule, joint cartilage and subchondral bone tissue), minimises its adverse effects at both local and systemic levels.

Intra-articular injection of the formulations according to the invention gives rise to long-acting therapeutic concentrations of stanozolol in the synovial fluid, and enables stanozolol to be carried regularly, for a long period, into the cytoplasm of the cells that make up the joint tissues (especially chondroblasts) with the aid of "nanocarriers" consisting of micelles of hyaluronic acid.

The nanocarrier micelles originating from the breakdown of hyaluronic acid bond to the CD44 receptors present on the chondroblast cell surface. It has been demonstrated that the CD44 receptors internalise in the cell cytoplasm hyaluronic acid micelles conjugated with bioactive molecules such as antiblastic medicaments (Qiu, L., et al., *RSC Advances* 6(46): 39896-39902). Specifically, the breakdown of stanozolol hyaluronate in the synovial fluid, supported by hyaluronidase, gives rise to hyaluronic acid micelles conjugated with stanozolol. Said nanocarrier micelles internalise stanozolol in the chondroblasts. Chondroblasts and synoviocytes do not normally produce hyaluronidase, but increased expression of hyaluronidase has been documented in the synovial fluid of patients suffering from osteoarthritis and rheumatoid arthritis (Yoshida M, et al., *Arthritis Research & Therapy*. 2004; 6(6):R514-R520. doi:10.1186/ar1223.). Under such conditions, the stanozolol hyaluronate formed by high-molecular-weight hyaluronic acid is broken down by the activity of hyaluronidase-2 into fragments of micellar dimensions (nanocarrier micelles) which can bond to the CD44 receptor and be internalised in the target cells. The activity of cytoplasmic esterases then determines the release of stanozolol into the chondroblasts.

The prevalent release of stanozolol into the cell cytoplasm, the elective site of action, is determined by the different esterase concentrations in the extracellular and intracellular environments.

Unlike the situation in plasma, where the relevant esterase activity (in the mouse: 89.5 nM/ml/sec; in the rabbit: 14.9 nM/ml/sec; in the pig: 7.0 nM/ml/sec) is believed to release much of the stanozolol conjugated with hyaluronic acid, in the absence of septic arthritis the esterase activity in the synovial fluid is reduced, so that only a negligible amount of stanozolol conjugated with hyaluronic acid can be released into the synovial fluid and enter the bloodstream, thus minimising the risk of systemic side effects.

The invention eliminates the main drawbacks of conventional devices because: (i) it uses a resorbable organic matrix as vector of a medicament with chondroregenerative activity, and (ii) it renders the medicament locally available at the optimum concentration required to promote tissue regeneration, reducing the systemic side effects almost to nil.

The concentration of the conjugates according to the invention in the formulations can vary within wide limits, depending on the application and the required dose of stanozolol. For example, the concentration could range between 0.1 and 15% by weight of the total hydrogel. The addition of 1% of the conjugate of the example to a saline solution increases its viscosity thousands of times, making it suitable for intra-articular administration; if the concentration is increased to 8-12%, the solution becomes a highly viscoelastic semisolid or solid body.

The invention is illustrated in detail in the examples below.

EXAMPLE 1

Synthesis of N-Fmoc-stanozolol (Fmoc-Stano)

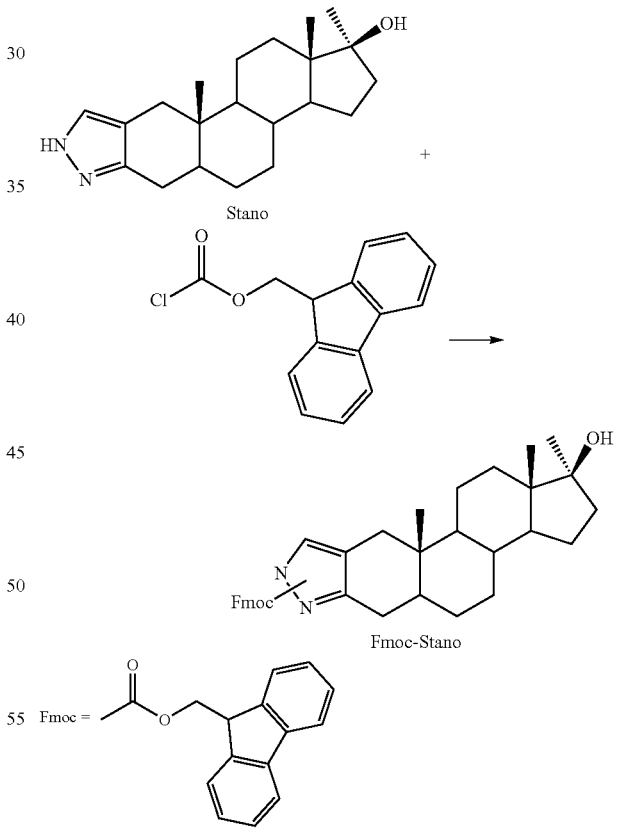

Stanozolol (100 mg, 0.305 mmols) was suspended in a mixture of tetrahydrofuran (2 mL), water (1 mL) and NaHCO$_3$ (30 mg). Fmoc chloride (158 mg, 0.61 mmols) was added to said mixture, and the reaction mixture was left at r.t. for 18 h. The tetrahydrofuran was then eliminated, and the remaining slurry was diluted with water (10 mL) and extracted with ethyl acetate (20 mL). The organic layer was washed with a 5% aqueous solution of NaHCO$_3$ (2×20 mL) and dried, and after removal of the solvent, the crude product was purified by column chromatography or crystallisation (petroleum ether/EtOAc). N-Fmoc-protected stanozolol was obtained as a mixture of two regioisomers (150 mg, 90%): (N-(fluorenylmethyloxycarbonyl)-17a-methylpyrazole[4', 5':2,3]-5a-androstan-17b-ol and N-(fluorenylmethyloxycarbonyl)-17a-methylpyrazole[3',4':3,2]-5a-androstan-17b-ol.

$^1$H-NMR resonances selected for the mixture of the two regioisomers (300 MHz, CDCl$_3$): selected $^1$H-NMR resonances (400 MHz, CDCl$_3$): δ 0.67 (s, 3H, 19-H one isomer), 0.78 (s, 3H, 19-H other isomer), 2.38 (dd, J=12.3, 17.1 Hz, 1H, 4-H other isomer), 2.50 (d, J=15.7 Hz, 1H, 1-H one isomer), 2.70 (d, J=15.8 Hz, 1H, 1-H other isomer), 7.52 (s, 1H, 2'-H one isomer), 7.77 (s, 1H, 2'H other isomer).

(N-(Fluorenylmethyloxycarbonyl)-17a-methylpyrazole [4',5':2,3]-5a-androstan-17b-ol (2-Fmoc isomer):

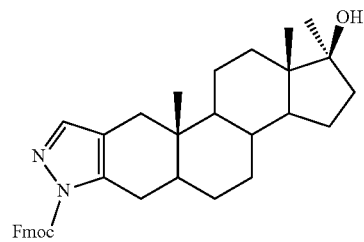

2-Fmoc isomer, selected $^1$H-NMR resonances (400 MHz, CDCl$_3$): δ 0.78 (s, 3H,19-H), 0.88 (s, 3H,18-H), 1.23 (s, 3H,20-H), 2.12 (d, J=15.5 Hz, 1 H,1-H), 2.38 (dd, J=12.3, 17.1 Hz, 1H, 4-H), 2.70 (d, J=15.8 Hz, 1H, 1-H), 2.77 (dd, J=5.1, 17.1 Hz, 1H, 4-H), 4.44 (t, J=xx Hz, 1H, Fmoc), 4.66 (d, J=xx Hz, 2H, Fmoc), 7.32 (t, J=xx Hz,2H, Fmoc), 7.43 (t, J=xx Hz, 2H, Fmoc), 7.66 (d, J=xx Hz, 2H, Fmoc), 7.77(s, 1H, 2'H), 7.80 (d, J=xx Hz, 2H, Fmoc)

N-(Fluorenylmethyloxycarbonyl)-17á-methylpyrazole[3', 4':3,2]-5á-androstan-17β-ol (1-Fmoc isomer):

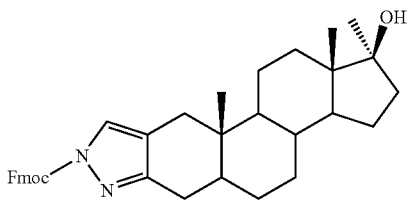

1-Fmoc isomer, selected $^1$H-NMR resonances (400 MHz, CDCl$_3$): δ 0.67 (s, 3H, 19-H), 0.87 (s, 3H, 18-H), 1.24 (s, 3H, 20-H), 2.50 (d, J=15.7 Hz, 1H, 1-H). 2.65 (dd, J=5.0, 17.8 Hz, 1H, 4-H), 4.42 (t, J=xx Hz, 1H, Fmoc), 4.75 (d, J=xx Hz, 2H, Fmoc), 7.33 (m, 2H, Fmoc), 7.41 (t, J=xx Hz, 2H, Fmoc), 7.52 (s, 1H, 2'-H), 7.69 (m, 2H, Fmoc), 7.78 (d, J=xx Hz, 2H, Fmoc).

EXAMPLE 2

Synthesis of bromo-butyric Derivative of N-Fmoc-stanozolol (Fmoc-Stano-Br)

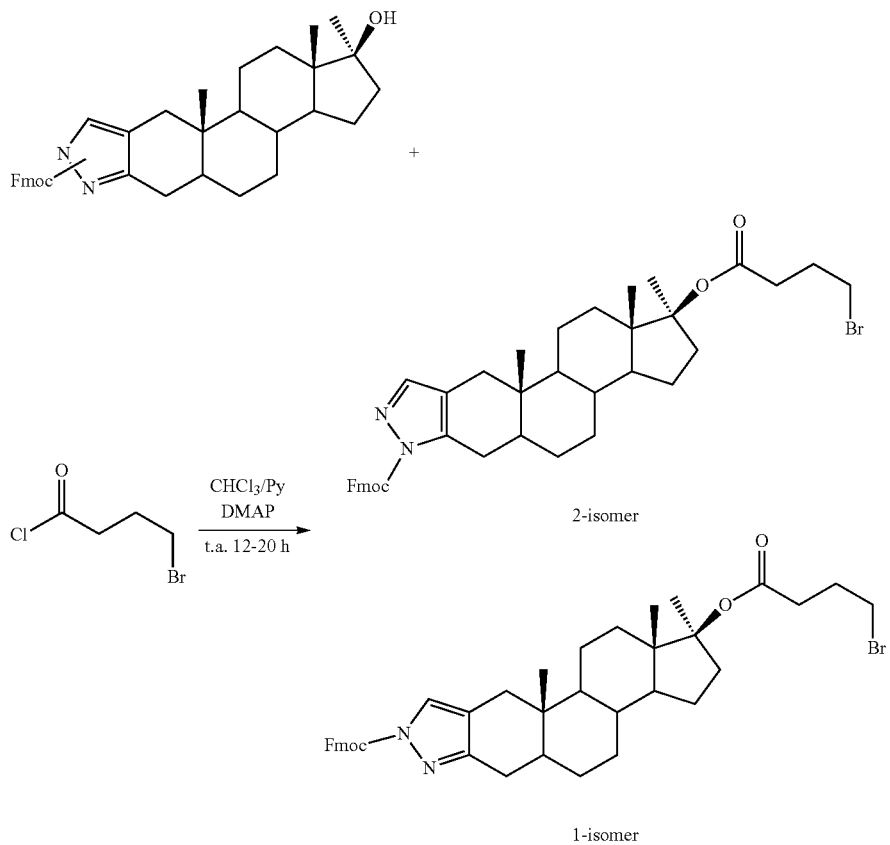

4-bromobutyryl chloride (0.350 mg, 3.04 mmols) and a catalytic amount of DMAP were added to a solution of Fmoc-Stano (mixture of regioisomers) (480 mg, 0.87 mmols) in $CHCl_3$ or $CH_2Cl_2$ (7 mL) and pyridine (0.245 mL, 3.04 mmols), and the reaction mixture was stirred overnight at room temperature. The mixture was then washed with 5% aqueous HCl (5 mL) and 5% $NaHCO_3$ (3×10 mL) and dried, and the solvent was removed in a vacuum to give the ester Fmoc-Stano-Br as a mixture of regioisomers (578 mg, 95%).

ESI-MS ($CH_3CN$/MeOH): m/z 723.27 (45%) $(M+Na)^+$, 1421 (100%) $(2M+Na)^+$ Selected $^1$H-NMR resonances (400 MHz, $CDCl_3$): δ 0.67 (s, 3H, 19-H, isomer 1), 0.78 (s, 3H,19-H, isomer 2), 0.86 (s, 3H,18-H, isomer 1), 0.87 (s, 3H,18-H, isomer 2), 1.43 (s, 3H, 20-H), 2.43 (t, J=6.9 Hz, 2H, CH2CO), 2.51 (d, J=15.2 Hz, 1H, 1-H, isomer 1), 3.46 (t, J=6.9 Hz, 2H, $CH_2Br$), 4.66 (d, J=7.6 Hz, 2H, Fmoc, isomer 2), 4.76 (dd, J=2.0, 7.6 Hz, 2H, Fmoc, isomer 1), 7.51 (s, 1H, 2'-H, isomer 1), 7.77 (s, 1H, 2'-H, isomer 2).

EXAMPLE 3

Synthesis of hyaluronic acid tetrabutylammonium salt (HA-TBA)

Sodium hyaluronan was converted to the tetrabutylammonium salt to increase its solubility in organic solvents: amberlite resin IR-120 in acid form (Sigma-Aldrich) was pre-converted to the tetrabutylammonium (TBA) form by treatment at 40° C. with a two-fold excess of a 40% w/w aqueous solution of TBA hydroxide (compared with the capacity of the resin). The resin in TBA form was then washed with distilled water to reduce the pH value below 8. The resin (1.1 mmols) was then transferred into a 1-2% (w/w) aqueous solution of HA-Na (0.2 mmols, i.e. moles of repeating dimer unit) under stirring for 40 h at room temperature. The resin was removed by filtration, and the solution was freeze-dried to obtain HA-TBA as a white solid to be stored in a cool place.

EXAMPLE 4

Synthesis of the hyaluronic acid-stanozolol Conjugate (HA-Stano)

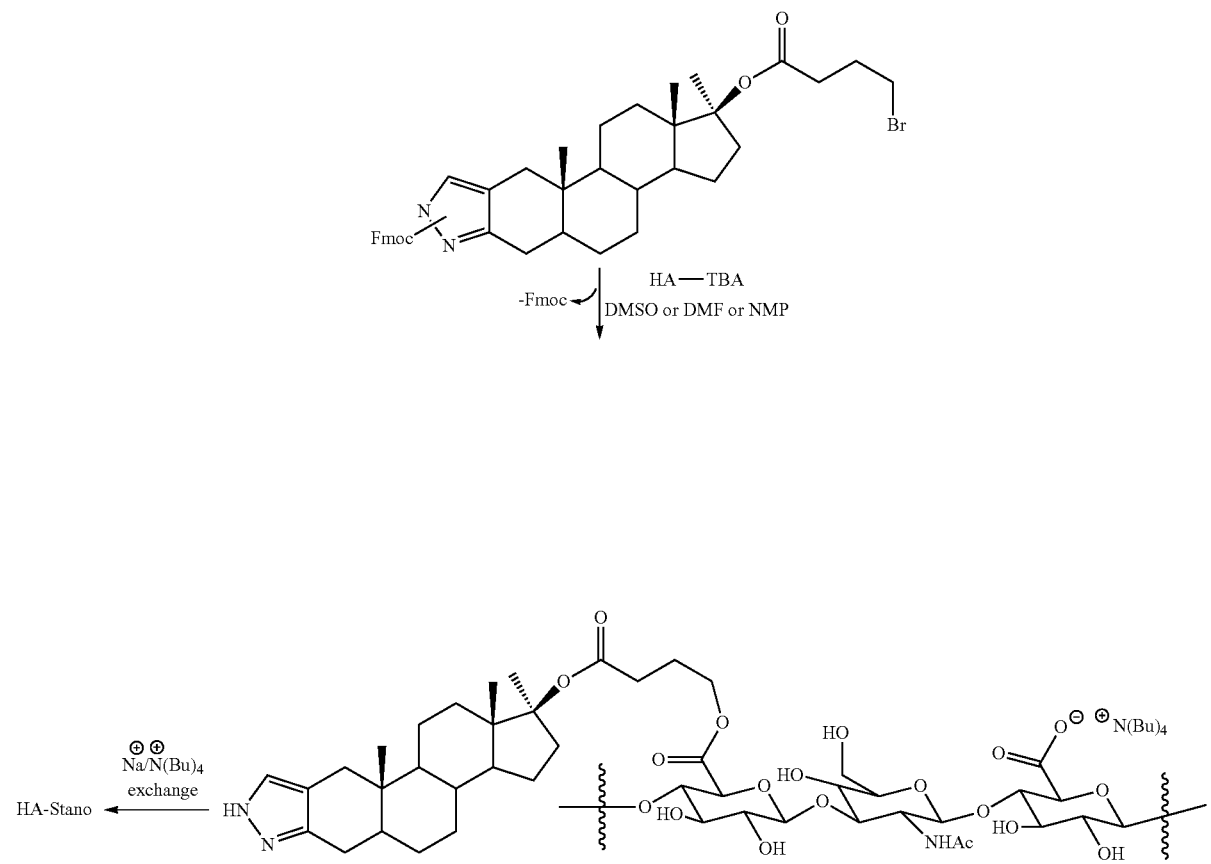

The derivative Fmoc-Stano-Br (22 mg) was added to a solution of 100 mg of HA-TBA in 2 mL of DMF (or NMP or DMSO) to obtain a degree of derivatisation HA-TBA of 20% moles. moles$^{-1}$ (mole of stanozolol per mole of repeating HA dimer unit). The reaction mixture was kept under magnetic stirring for 48 h at 40° C. The product HIALUSTAN was obtained as a white solid by adding acetone, followed by Na/TBA exchange on a Dowex resin (form Na$^+$). The HA-Stano conjugate was characterised with $^1$H-NMR spectra (400 MHz) in DMSO-d$_6$/D$_2$O and IR.

The invention claimed is:

1. Conjugate between a therapeutic effective amount of stanozolol and hyaluronic acid or a hyaluronic acid salt, wherein stanozolol is conjugated with the carboxylic group of hyaluronic acid or of the hyaluronic acid salt via a spacer which forms an ester bond with the hydroxyl group of stanozolol and an ester or amide bond with the carboxyl group of hyaluronic acid or of the hyaluronic acid salt.

2. Conjugate according to claim 1, wherein the conjugation degree of hyaluronic acid ranges between 1 and 90% mol/mol with respect to the number of repeating dimeric units of hyaluronic acid or the salt thereof.

3. Conjugate according to claim 1, of formula (I)

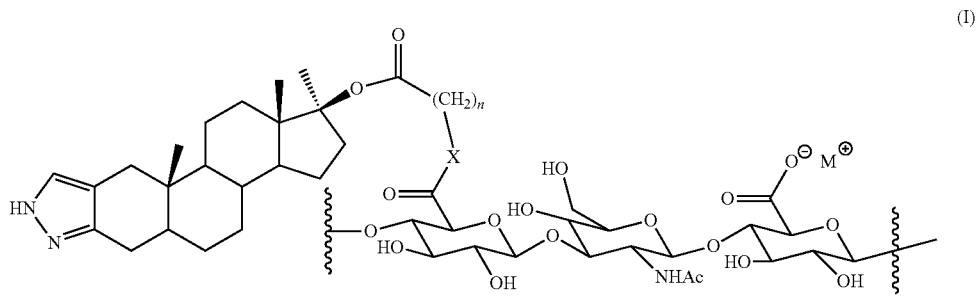

wherein:
n=1-12;
X is a bivalent group selected from —O— and —NH—;
M$^+$ is an alkali metal proton or cation;
the group

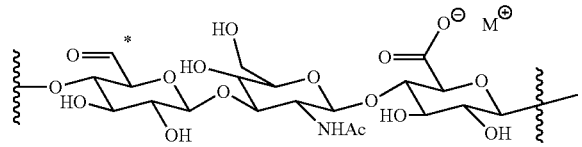

is the repeating unit of hyaluronic acid or of an alkali metal salt thereof, wherein the symbol * indicates the carbon atom of said repeating unit bonded to the X group.

4. Conjugate according to claim 3, wherein X is the group —O—.

5. A pharmaceutical and veterinary composition comprising the conjugate of claim 1 in admixture with at least one carrier or excipient.

6. The pharmaceutical and veterinary composition according to claim 5 in the form of hydrogels, injectable hydrogels, hydrogels for external use, creams, lotions, foams, aqueous solutions for intra-articular use, emulsions for ophthalmic use, or eye drops.

7. Scaffolds, artificial tissues and culture media comprising the conjugate of claim 1.

* * * * *